United States Patent [19]

Knauf

[11] Patent Number: 4,713,351

[45] Date of Patent: Dec. 15, 1987

[54] MONOCLONAL ANTIBODY DIRECTED TO AN ANTIGEN DERIVED FROM HUMAN OVARIAN TUMORS AND A RADIOIMMUNOASSAY USING THE ANTIBODY

[75] Inventor: Suzanne Knauf, Fairport, N.Y.

[73] Assignee: The University of Rochester, Rochester, N.Y.

[21] Appl. No.: 817,317

[22] Filed: Jan. 9, 1986

Related U.S. Application Data

[63] Continuation-in-part of Ser. No. 461,770, Jan. 28, 1983, Pat. No. 4,584,278, which is a continuation-in-part of Ser. No. 360,238, Mar. 19, 1982, abandoned.

[51] Int. Cl.[4] .......................................... G01N 33/536
[52] U.S. Cl. ...................................... 436/542; 456/548

[58] Field of Search ................................ 436/514–516, 436/536–547, 63, 64, 804, 813, 815, 825, 828, 548; 435/7; 424/1.1; 260/112 R

[56] References Cited

U.S. PATENT DOCUMENTS 4,584,278  4/1986  Knauf ................................ 436/542

Primary Examiner—Deborah L. Kyle
Assistant Examiner—T. J. Wallin
Attorney, Agent, or Firm—Martin Lukacher

[57] ABSTRACT

A monoclonal antibody directed to an antigen, named NB/70K, derived from human ovarian carcinomas and a radioimmunoassay for the detection of ovarian carcinomas using said monoclonal antibody.

4 Claims, 3 Drawing Figures

MONOCLONAL ANTIBODY DIRECTED TO AN ANTIGEN DERIVED FROM HUMAN OVARIAN TUMORS AND A RADIOIMMUNOASSAY USING THE ANTIBODY

DESCRIPTION

This application is a continuation in-part-of my co-pending application Ser. No. 461,770, now U.S. Pat. No. 4,584,278 filed Jan. 28, 1983, which is a continuation-in-part of my then co-pending application Serial No. 360,238 filed Mar. 19, 1982 (now abandoned).

The present invention relates to the development of a monoclonal antibody, named NB12123, directed to NB/70K, and relates to an improved radioimmunoassay using NB12123 to detect the presence and level of NB/70K in a patient's serum.

NB/70K is a unique fraction isolated from ovarian tumor homogenates. It is specific for ovarian carcinomas. NB/70K is useful in preparing anti-NB/70K, a polyclonal antibody, which may be used in a radioimmunoassay. The assay can serve as a diagnostic tool in the detection and monitoring of ovarian carcinomas. The antigen and polyclonal antibody are more fully described in my co-pending application Ser. No. 461,779, now U.S Pat. No. 4,584,278.

A drawback to any assay using anti-NB/70K exists because of the presence of an inhibitory factor that is present in normal plasma. This inhibitory factor was recently discovered, is a glycoprotein and has a molecular weight only slightly larger than NB/70K. It has been named NB/70K inhibitor (or "NPIF"). NPIF, although it will not bind to anti-NB/70K, will inhibit the binding of NB/70K to anti-NB/70K. As a result, the "false negative" rate among ovarian cancer patients is close to 50%.

To avoid the effect of "false negatives" in the detection of ovarian cancer, a monoclonal antibody was sought which would not bind to NPIF, which would bind to NB/70K in a manner unaffected by the presence of NPIF and which would be useful in a radioimmunoassay capable of measuring NB/70K in unextracted serum. A monoclonal antibody with such characteristics and a radioimmunoassay using the antibody have been developed.

The features and advantages of the invention as well as the best known mode for practice thereof will become more apparent from a reading of the following detailed description which makes reference to the following drawings.

To make a monoclonal antibody specific for NB/70K, BALB/cBy mice (available from Jackson Laboratory, Bar Harbor, Me.) were immunized with 20 ug NB/70K in Freund's complete adjuvant. The mice were boosted on three days prior to fusion. The mice were tested for production of antibodies to NB/70K and NPIF as described below.

Immune splenocytes from mice whose immune systems produced antibodies to NB/70K and NPIF were fused with log phase P3/x63.Ag 8/653 myeloma cells in the presence of polyethylene glycol 1500 according to methods known to those skilled in the art. A small amount of the fusate was cultured directly. Supernatants from those cells which exhibited growth again were tested for production of antibodies to NB/70K and NPIF (also as described below). Cells from wells which tested positively were cloned twice by limiting dilution.

Supernatant from large cultures of stable clones were tested by radioimmunoassay for binding to $I^{125}$ NB/70K. Clones with high levels of monoclonal antibody against NB/70K and a high degree of affinity for NB/70K then were tested against NPIF. Clones which did not exhibit inhibition in the binding of NB/70K to the monoclonal antibody in the presence of excess NPIF were finally chosen.

Balb/c mice then were primed with Pristane (TM-generically referred to as 2, 6, 10, 14-tetramethylpentadecane, and available from Sigma Chemical Co.) by intraperitoneal injection 6 days before injection of $2-6 \times 10^6$ cells from the final chosen clones. Ascites from immunized mice were centrifuged to remove cells and clarify the supernatant. Several monoclonal antibodies, NB2231, NB8412, NB12123, NB12913, NB13831, NB16953, NB17134 and NB17434 produced by this method were isolated from the supernatant. They have been deposited with Dr. Edith M. Lord at the University of Rochester and are available therefrom.

All of the monoclonal antibodies isolated and identified above have the characteristics described above. One antibody, NB12123, was chosen for further study; however, any of these above antibodies could be substituted therefor in the following procedures.

Figure 1:
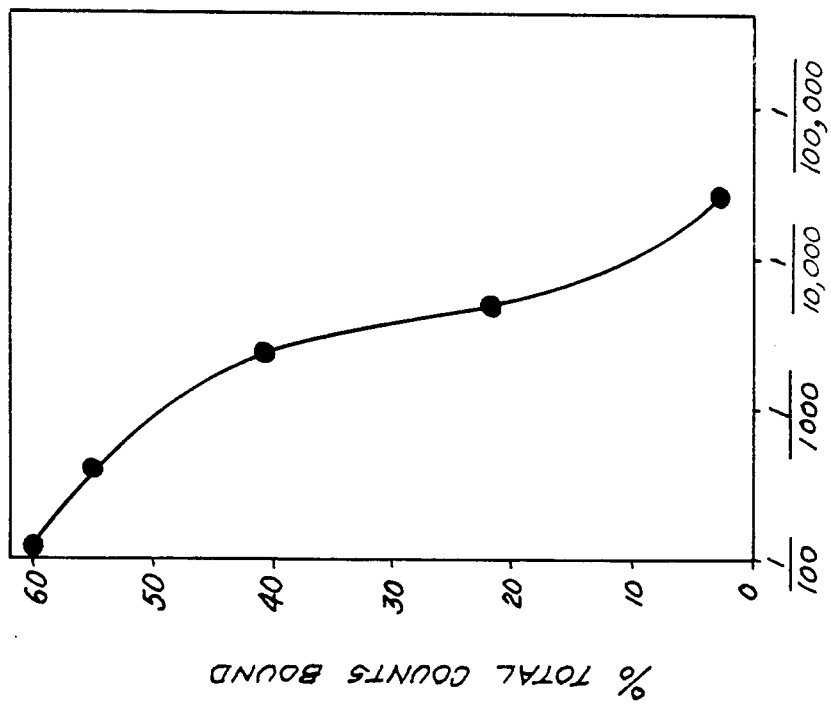
FIG. 1 is plot of the percent of total $I^{125}$ NB/70K counts bound versus a dilution of NB12123.

NB12123 was titrated with $I^{125}$ NB/70K. The resulting curve is presented in FIG. 1. This shows that the amount of $I^{125}$ NB/70K bound to antibody is proportional to the amount of antibody present.

Radiolabelled NB/70K also was absorbed with either NB12123 or anti-NB/70K and the binding of absorbed antigen to antibody was measured. Essentially all of the antigen capable of binding to NB12123 was bound to the anti-NB/70K aosorbent. Only a fraction of the antigen capable of binding to anti-NB/70K remained after absorption with the NB12123 absorbant. This indicates that most of the NB/70K molecules which carry the antigenic determinants recognized by the monoclonal NB12123 also carry the determinants recognized by the polyclonal anti-NB/70K.

An improved radioimmunoassay, the NB12123 assay, was developed to detect the presence of and to measure the level of NB/70K in a sample. Fifty ul of a 1:10 dilution of serum taken from a patient by venipuniture was added to a dilution of NB12123 in phosphate buffered saline ("PBS") containing 2% normal rabbit serum in a 10×75 mm test tube. Normal rabbit serum is necessary because it non-specifically increases the binding of antigen to antibody. After incubation at 37° C. for 15 minutes, 20 ul of $I^{125}$ NB/70K in Triton-EDTA buffer, containing additional Triton, was added to the test tube. After incubation at 37° C. for one hour, the tubes were transferred to an ice bath and 200 ul of a precipitating mixture was added. The precipitating mixture was Pansorbin (TM-generically referred to as *Staphylococcus aureus* of the Cowan I strain bearing protein A, and available from CalBiochem, La Jolla, Calif.) (2.5% v/v)

and rabbit anti-mouse globulin coupled to Pansorbin (5% v/v) in the 0.1% Triton-EDTA buffer previously described in Ser. No. 461,770. Use of this precipitating mixture was necessary to insure that all subclasses of murine immunoglobulin were precipitated.

After incubation at 4° C. for one hour or overnight, 2 ml of ice cold PBS was added, the tubes were centrifuged at 1500g for 30 minutes and the supernatants decanted. The pellets were counted for one minute in a gamma counter.

In order to develop a standard curve for this assay, Fractions OCC, OCA, OCB or OCD or NB/70K to which 5 ul of pooled normal serum have been added may be substituted for the patient's serum to be tested. Appropriate dilutions of these standard antigen preparations to give 0-200 AU of NB/70K activity may be used.

This assay may be modified to test culture supernatants for the presence of antibody against NB/70K. A volume of culture supernatant was added to tne 20 ul of labeled antigen and the assay is followed from that point. To test for NPIF, labeled NPIF was substituted for labeled NB/70K.

Figure 2:
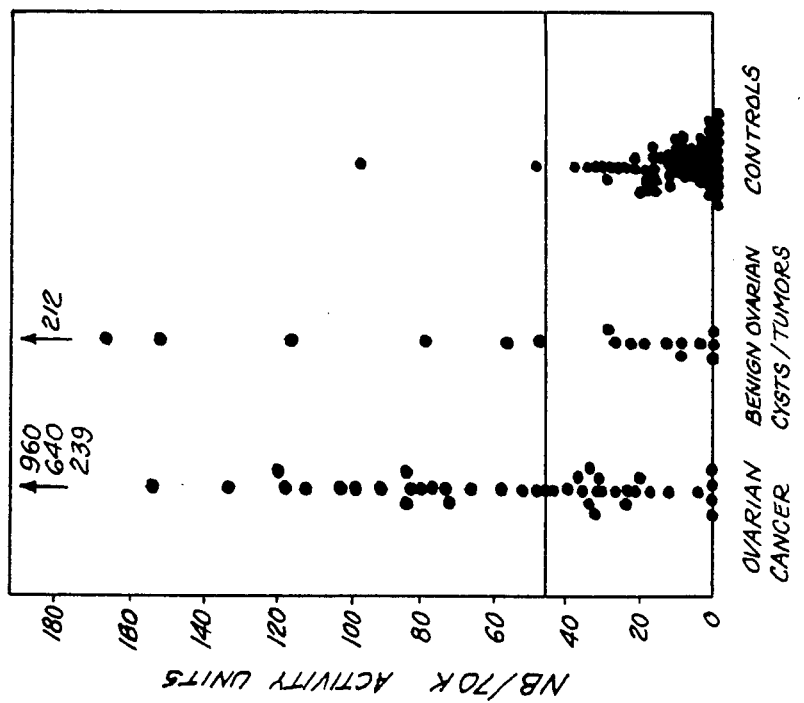
FIG. 2 is a bar graph showing the NB/70K activity level in serum taken from pretreatment/preoperative patients who then were catagorized after surgery on the basis of their condition.

The NB12123 assay was used to measure NB/70K levels in pretreatment/preoperative serum from ovarian cancer patients and controls. The average NB/70K value for 75 serum samples ootained from normal, healthy blood donors was 11.9 AU with a standard deviation (S.D.) of 14.9 AU. The upper limit of normal was therefore set at 45 AU (mean +2S.D.). Using this level, 2 of the 75 control samples (3%) had elevated serum NB/70K levels. An additional 10 patients who were suspected to have gynecologic tumors but who were determined to be tumor-free upon surgical exploration all had NB/70K levels below 45 AU with an average NB/70K level of 12.2 AU. Serum NB/70 levels were measured in 18 patients with benign ovarian cysts or tumors and 46 patients with ovarian cancer (FIG. 2). Seven of the 18 patients (39%) witn benign ovarian cysts or tumors and 24 of 46 (52%) ovarian cancer patients had elevated serum NB/70K levels. The average serum NB/70K value for ovarian cancer patients was 90.7 AU compared to 54.0 AU for the patients with benign ovarian cysts or tumors and to 11.9 AU and 12.2 AU in the no disease control groups.

Ovarian cancer patient serum NB/70K levels measured in the NB12123 assay were compared with NB/70K levels measured in the Triton NB/70K assay as described in Ser. No. 461,770. (See Table A). NB/70K activity in the equivalent of 5 ul of serum in the NB12123 assay and 0.2 ul of serum in the Triton NB/70K assay were measured. Evaluation of standard preparations of NB/70K indicated that 1 "AU" as measured by NB12123 assay was equivalent to the activity of 11.5 "U" as measured in the Triton NB/70K assay.

TABLE - A

Comparison of serum NB/70K activity in ovarian cancer patients measured by radioimmunoassay using polyclonal and monoclonal antibodies against NB/70K

| Patient Monoclonal | NB/70K Value | | Rank[3] | |
|---|---|---|---|---|
| | Polyclonal[1] | 1 Monoclonal[2] | Polyclonal | Monoclonal |
| L. H. | 73 U | 119 AU | 1 | 5 |
| H. V. | 59 | 100 | 2 | 7 |
| D. L. | 51 | 640 | 3 | 2 |
| K. C. | 34 | 82 | 4 | 10 |
| C. M. | 34 | 118 | 5 | 6 |
| F. K. | 28 | 58 | 6 | 11 |
| A. B. | 27 | 960 | 7 | 1 |
| C. C. | 15 | 92 | 8 | 8 |
| E. T. | 14 | 155 | 9 | 4 |
| B. M. | 13 | 32 | 10 | 17 |
| E. M. | 8 | 83 | 11 | 9 |
| C. S. | 7 | 239 | 12 | 3 |
| J. M. | 5 | 0 | 13 | 18 |
| N. B. | 0 | 46 | 14 | 12 |
| E. H. | 0 | 44 | 14 | 13 |
| A. C. | 0 | 37 | 14 | 14 |
| L. W. | 0 | 36 | 14 | 15 |
| J. T. | 0 | 35 | 14 | 16 |
| M. G. | 0 | 8 | 14 | 18 |
| E. W. | 0 | 0 | 14 | 18 |
| H. T. | 0 | 0 | 14 | 18 |
| Mean | 17.5 U | 137.3 AU | | |
| Range | 0-73 U | 0-960 AU | | |

[1]Expressed as units "U" per 50 ul of a 1:250 dilution of sample; rabbit anti-NB/70K, #902-3; Triton NB/70K assay.
[2]Expressed as units "AU" per 50 ul of a 1:10 dilution of sample; monoclonal anti-NB/70K NB12123; NB12123 assay.
[3]Ordered from highest to lowest NB/70K activity.

In 21 patient samples examined, values ranged from 0 to 73 U in the Triton assay and from 0 to 960 AU in the NB12123 assay. Wnen patients were ranked from highest to lowest serum NB/70K levels, the rank of patients in the two assays was different. Ten of 21 (48%) patients had elevated NB/70K levels using a 10 U cutoff in the Triton assay. Twelve of the 21 (57%) patients had elevated NB/70K levels using a 45 AU cut-off in the NB12123 assay. These results indicate the monoclonal assay was only slightly better than the polyclonal assay for detecting elevated serum NB/70K levels in ovarian cancer patients. However, the much greater range of values obtained in the monoclonal assay indicated a greater sensitivity of this assay for detecting differences in serum NB/70K levels.

The two assay systems appear to measure different sets of antigenic determinants as evidenced by the differences apparent in Table A. Studies of 56 serum samples examined in both the Triton and NB12123 assays indicated a correlation coefficient of 0.403. The correlation coefficient of NB/70K levels as measured by the two assays for only the ovarian cancer patient samples (n=21) was 0.388. Although there was no correlation between the absolute NB/70K values measured by the two assays, 9 patients had elevated NB/70K in both assays. Three patients nad normal "U" values and high "AU" levels while only one patient had normal "AU" levels and elevated "U" levels.

Figure 3:
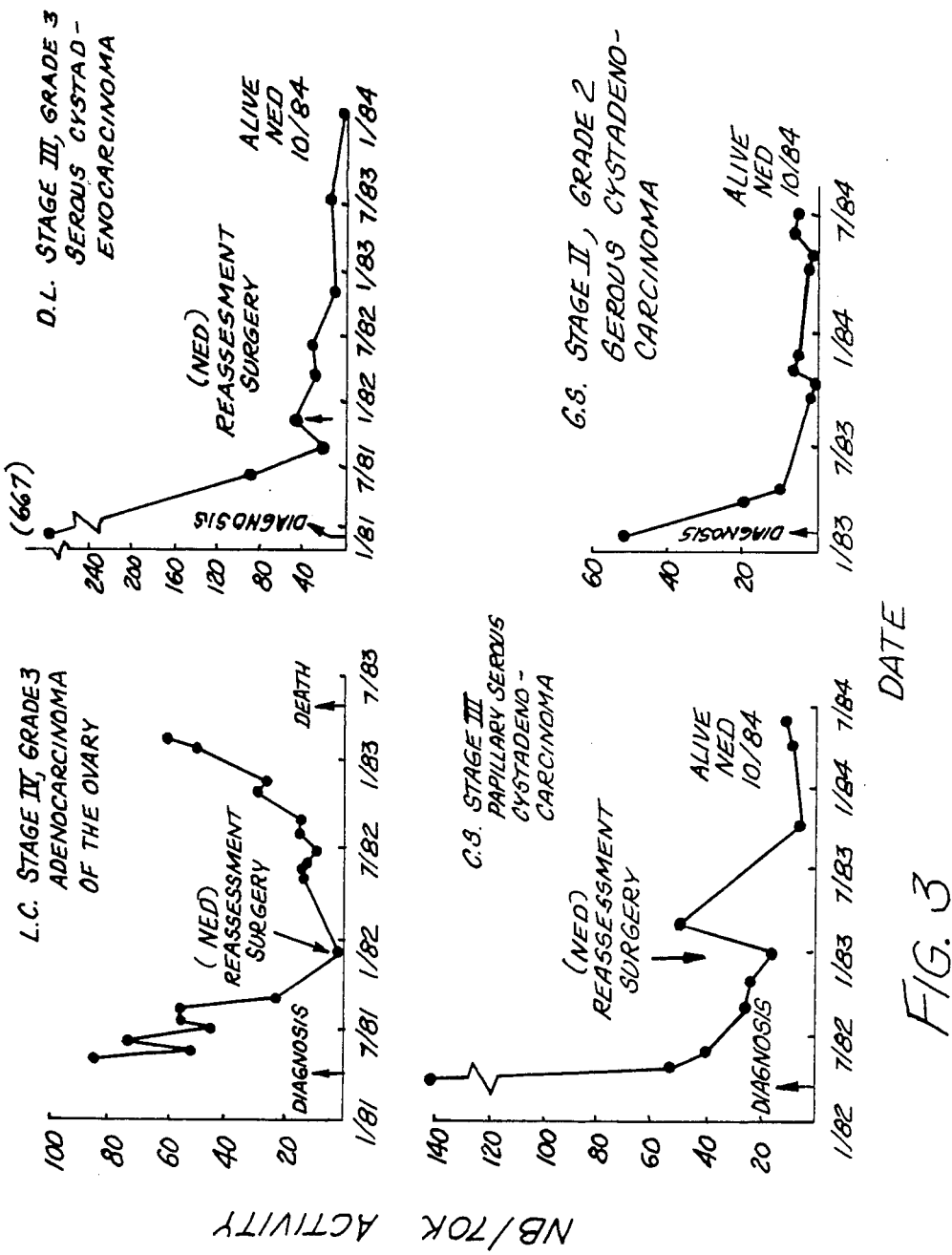
FIG. 3 is a plot NB/70K activity versus time for four post-operative/post-treatment patients having ovarian cancer.

Serum NB/70K levels in serial samples from four ovarian cancer patients were determined using the NB12123 assay (FIG. 3). In tnese four patients, decreasing serum NB/70K levels indicated a reduction in tumor burden and consistently low NB/70K levels indicated a favorable prognosis. The three patients who underwent reassessment surgery all had low serum NB/70K levels and no evidence of residual tumor as determined clinically and histologically at the time of surgery. In the one patient who died, serum NB/70K levels steadily increased during the year preceeding her death. The other three patients have had consistently low NB/70K levels and are alive with no evidence of disease after as much as three years after diagnosis of ovarian cancer. Such results indicate that the NB12123 assay has sufficient sensitivity for the monitoring of ovarian cancer patients.

Differences in the ability of the polyclonal and monoclonal assays to detect serum NB/70K may also be the result of differences in the ability of the NPIF to inhibit antigen-antibody binding. The polyclonal assay is sensitive, while the NB12123 assay is insensitive to inhibition by NPIF. In addition, the non-NPIF inhibitable epitope against which NB12123 is directed may not be the only tumor epitope expressed by malignant tumors. A panel of assays, each using a different monoclonal antibody against a different epitope of NB/70K, may be necessary before the specificity and sensitivity of NB/70K for ovarian cancer can be demonstrated using monoclonal antibodies as it was shown for polyclonal antibodies. By selecting several monoclonal antibodies, each of which recognizes a different epitope, a plurality of assays (as descrioed for NB12123) can be run in order to eliminate the possibility of obtaining a "false negative" or "false positive" reading from any single assay.

Comparison of NB/70K levels determined for the same serum samples in both the polyclonal and NB12123 assays indicated that, although both assays had approximately the same percentage of positive samples, there appeared to be no correlation oetween the absolute NB/70K levels measured by the two assays, even if differences in units of NB/70K activity and sample size between the two assays are considered. The range of NB/70K values in the NB12123 assay was much greater than that in the polyclonal assay, indicating greater sensitivity of the monoclonal assay. In addition, the rank of ovarian cancer patient samples was different for the two assays, suggesting that the two assays do not measure exactly the same set of antigenic determinant(s), even though there may be overlap between the two sets.

Variations and modifications in the herein described method, antigen, antibody and radioimmunoassays, within the scope of the invention may negate themselves to those skilled in the art. Accordingly, the foregoing descriptions should be taken as illustrative and not in a limiting sense.

I claim:

1. An improved radioimmunoassay, the NB12123 assay, to detect the presence of an ovarian tumor specific antigen, NB/70K, and the amount of NB/70K present, comprising tne steps of isolating Fraction OCC, OCA, OCB or OCD or NB/70K or serum, adding said isolate to a dilution of NB12123 in PBS containing 2% normal rabbit serum in a container, allowing sufficient time for said monoclonal antibody to react with said isolate, after said time has expired adding a radioiodinated NB/70K to said container, allowing a sufficient time for said radioiodinated NB/70K to react with a complex of monoclonal antibody and isolate, adding a mixture of *Staphylococcus aureus* of the Cowan I strain bearing protein A, 2.5% (v/v), and raboit anti-mouse globulin coupled to *Staphylococcus aureus* of the Cowan I strain bearing protein A, 5% (v/v), in the Triton-EDTA buffer to said container, centrifuging the container, decanting the supernatant and counting the radioactivity of the resulting pellet.

2. The radioimmunoassay as set forth in claim 1 wherein NB/70K is iodinated by the chloramine T method and labeled NB/70K is separated from unbound $I^{125}$ by dialysis in PBS.

3. The radioimmunoassay as set forth in claim 1 wherein serum is isolated from blood samples taken from individuals.

4. The radioimmunassay as set forth in claim 1 wherein a monoclonal antibody selected from the group consisting of NB2231, NB8412, NB12913, NB13831, NB16953, NB17134 and NB17434 is substituted for NB12123. 7

* * * * *